United States Patent [19]

Giroux et al.

[11] 4,210,664
[45] Jul. 1, 1980

[54] USE OF α,α'-DITHIOBIS(β-ARYLACRYLIC ACID) DERIVATIVES TO ENHANCE ZINC SERUM AND TISSUE CONCENTRATIONS

[75] Inventors: Eugene L. Giroux, Cincinnati, Ohio; Nellikunja J. Prakash; Paul J. Schechter, both of Strasbourg, France

[73] Assignee: Merrell Toraude et Compagnie, Strasbourg, France

[21] Appl. No.: 16,942

[22] Filed: Mar. 2, 1979

[51] Int. Cl.$^2$ .................. A61K 31/19; A61K 31/34; A61K 31/38; A61K 31/40
[52] U.S. Cl. .................. 424/275; 424/274; 424/285; 424/317
[58] Field of Search .............. 424/274, 275, 285, 317

[56] References Cited

U.S. PATENT DOCUMENTS 4,124,718  11/1978  Giroux et al. .................. 424/274

OTHER PUBLICATIONS

Haskell, et al., J. Med. Chem. 13, 697, (1970).
Campaigne, et al., J. Org. Chem. 21, 32, (1956).
Schneller, et al., C.A., vol. 81, (1974), 37492k.

*Primary Examiner*—Allen J. Robinson
*Attorney, Agent, or Firm*—Stephen L. Nesbitt; L. Ruth Hattan; Eugene O. Retter

[57] ABSTRACT

This invention relates to a novel method for enhancing zinc serum and tissue concentrations which comprises administering a compound of the formula:

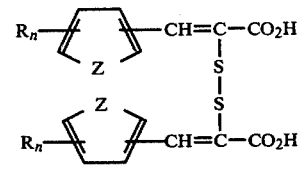

wherein Z is C=C, O, S, NH; R is hydrogen, methyl, ethyl, hydroxy, methoxy, ethoxy, chlorine, bromine, fluorine, iodine or trifluoromethyl; and n is 1, 2 or 3.

5 Claims, No Drawings

USE OF α,α'-DITHIOBIS(β-ARYLACRYLIC ACID) DERIVATIVES TO ENHANCE ZINC SERUM AND TISSUE CONCENTRATIONS

BACKGROUND OF INVENTION

While α,α'-dithiobis(β-arylacrylic) acids are known, their utilization in therapeutics is quite rare. The compounds employed in the present invention are most commonly prepared by the procedures of E. Campaigne and R. Cline, J. Org. Chem. 21, 32 (1956) by oxidation of the corresponding α-mercapto-β-arylacrylic acids. Haskel et al., J. Med. Chem. 13, 697 (1970) has prepared and tested α,α'-dithiobis[β-(2-thienyl)acrylic acid] and α,α'-dithiobis[β-(2-chlorophenyl)acrylic acid] for neuraminidase inhibition activity. The use of the α-mercapto-β-arylacrylic acids in combatting heavy metal poisoning, in treating hypertension, and in zinc serum and tissue concentration enhancement is disclosed in copending U.S. application Ser. No. 892,187, filed Mar. 31, 1978, allowed Jan. 15, 1979, to be issued Sept. 25, 1979, in U.S. Pat. No. 4,130,653 issued Dec. 19, 1978, and in U.S. Pat. No. 4,124,718 issued Nov. 7, 1978, respectively. No references more pertinent than these are known to the applicants.

SUMMARY OF THE INVENTION

This invention relates to a method of enhancing the serum zinc and tissue zinc concentrations in a patient in need thereof by administering an α,α'-dithiobis(β-arylacrylic acid) of Formula I or a pharmaceutically acceptable non-toxic salt thereof:

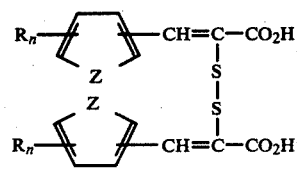

Formula I wherein Z is —C=C—, O, S or NH; R is H, $CH_3$, $C_2H_5$, OH, $CH_3O$, $C_2H_5O$, Cl, Br, F, I or $CF_3$; and n is 1, 2 or 3.

DETAILED DESCRIPTION OF THE INVENTION

It is apparent from the foregoing general Formula I that the compounds employed in the present invention are α,α'-dithiobis(β-thienylacrylic acids),
α,α'-dithiobis(β-furylacrylic acids),
α,α'-dithiobis(β-pyrrylacrylic acids),
α,α'-dithiobis-(β-phenylacrylic acids), and their pharmaceutically acceptable non-toxic salts thereof wherein the aromatic ring, that is, the thienyl, furyl, pyrryl or phenyl rings may be further substituted with from 1 to 3 groups selected from methyl, ethyl, hydroxy, methoxy, ethoxy, chlorine, bromine, fluorine, iodine or trifluoromethyl as illustrated, respectively, by the following Formulas II to V.

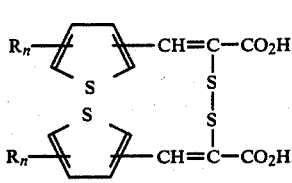

Formula II

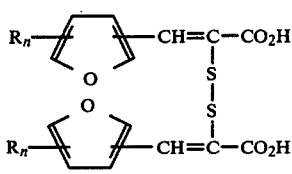

Formula III

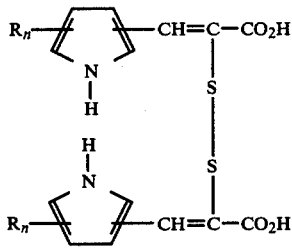

Formula IV

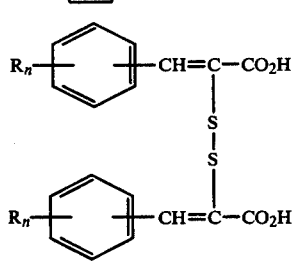

Formula V

In the above general Formulas II to V, R and n have the meanings defined in Formula I.

In general Formulas II and III it is preferred that the acrylic acid moiety, that is

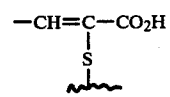

be attached to the 2-position of the furan or thiophene ring, and it is more preferred that within these groups of compounds when R is other than hydrogen that n be equal to 1 with the substituent as represented by R being attached at the 5-position of the furan or thiophene ring in the practice of the present invention. In general Formulas I to V, preferred substituent groups as represented by R are hydrogen, methyl, ethyl, hydroxy, methoxy, ethoxy, chlorine, bromine and trifluoromethyl.

Illustrative species within the general Formula I are compounds wherein the aryl group is phenyl or substituted phenyl, for example, 2-, 3- or 4-methyl, 2-, 3- or 4-ethyl, 2-, 3- or 4-bromo, 2-, 3- or 4-chloro, 2-, 3- or 4-fluoro, 2-iodo, 2,4-dichloro, 2,3-dichloro, 2,3,4-trichloro, 2-trifluoromethyl, 3-trifluoromethyl, 2-trifluoromethyl-3-chloro, 2-, 3- or 4-hydroxy, 2-, 3-or 4-methoxy, 2-, 3- or 4-ethoxy, 2-hydroxy-3-methoxy, 3-hydroxy-4-methoxy, 3-methoxy-4-hydroxy, 3-ethoxy-4-hydroxy, 2,3-dimethoxy, 2,4-dimethoxy, 2,5-dimethoxy, 2,6-dimethoxy, 3,4-dihydroxy, 3,4,5-trimethoxy, 2,3,4-trimethoxy, 3,5-dibromo-4-hydroxy; or other aryl groups in place of phenyl, namely, 2-furyl, 5-trifluoro-2-furyl, 5-methyl-2-furyl, 5-ethoxy- or 5-methoxy-2-furyl, 5-chloro-2-furyl; 3-furyl; 2-thienyl, or substituted thienyl, for example, 3-methyl, 5-methyl, 5-ethyl, 5-chloro, 5-bromo, 3-methoxy, 5-methoxy; 3-thienyl; 2-pyrryl; and 3-pyrryl; and pharmaceutically acceptable non-toxic salts thereof illustratively, sodium, potassium, calcium, aluminum, zinc, ammonium salts, amine salts, for example, trialkylamine, such as triethylamine, dibenzylamine, glucosamine, of each of the above acids.

The present invention provides a method of elevating the serum and tissue levels of zinc in patients in need thereof. Enhanced zinc levels has been indicated in the treatment of burns, serious intestinal fistulas, infarctions, malabsorption, wounds, surgery, dental extraction wounds, idiopathic hypogeusia, venous leg ulcers, decubitus ulcers, syndrome of dwarfism and hypogonadism. Raising the zinc serum and tissue level is indicated and has been effective in ameliorating or eliminating some of the disease condition or accelerating healing associated with regional enteritis, sickle cell anemia and disease, rheumatoid arthritis, acrodermatitis enteropathica, peptic ulcers, porphyria, hepatic cirrhosis, bone healing, psoriasis, postintubation tracheal granuloma, acute myocardial infarction, renal disease, anemia and geophagia, diabetis mellitus, thalassemia, oral contraception with estrogens, cystic fibrosis, Down's syndrome, pernicious anemia, or corticosteroid antiinflammatory use. Compounds of Formula I can efficaciously be administered to patients in need of zinc therapy as indicated above and wherever zinc therapy and enhanced zinc serum and tissue levels would be useful.

The most preferred embodiment of this invention is the use of the compounds of general Formula I or a pharmaceutically acceptable salt thereof wherein R is hydrogen in the treatment of disease conditions associated with lower than normal zinc serum and tissue levels.

As used herein the term patient is taken to mean warm blooded animals, for example, birds such as chickens and turkeys and mammals such as primates, humans, sheep, horses, bovine cows and bulls, pigs, dogs, cats, rats and mice in need of zinc therapy.

In practicing the present invention the compounds of Formula I or a salt thereof either alone or in combination with acceptable pharmaceutical carriers are administered to the patient to be treated either orally, parenterally, for example, subcutaneously or intravenously or topically. Compounds of general Formula I may be used in combination with one another. A preferred mode of administration of the compounds of general Formula i in the practice of the present invention is oral administration.

The compounds of Formula I may be formulated for oral administration as solid or liquid unit dosage forms. The solid dosage forms can be tablets, coated or uncoated; capsules, hard or soft; powders; granules; pills, enteric coated if desired. Solid diluents and carriers may be lactose, starch or other innocuous material with the usual tableting adjuncts as desired. Liquid oral compositions may be dispersions, suspensions, elixirs, syrups or simple solutions in aqueous vehicle. Polyethylene glycols including polyethylene glycol 300 have been found convenient oral vehicles. The term unit dosage form as used in the specification and claims means physically discrete units suitable for unitary administration, each unit containing a predetermined quantity of active ingredient to achieve the desired therapeutic effect in association with the pharmaceutical carrier. Sterile, intraperitoneal formulation with physiologically acceptable vehicle, for example, saline, optionally buffered can also be utilized.

The amount of compound administered will vary over a wide range depending upon the patient to be treated and the severity of the disease condition and will be any amount effective in enhancing zinc serum and tissue concentrations in patients in need thereof from about 0.1 mg/kg to 20 mg/kg of body weight of the patient per day. For example, a unit dosage form may suitably contain about 250 mg of active ingredient as represented by Formula I or a salt thereof.

The utility of the compounds of general Formula I in elevating zinc serum and tissue levels has been demonstrated in test rats given oral doses of the compounds of Formula I. Elevation in plasma zinc concentration as well as kidney and liver tissue zinc concentration was observed.

The $\alpha,\alpha'$-dithiobis($\beta$-arylacrylic acids) are more stable than the corresponding $\alpha$-mercapto-$\beta$-arylacrylic acids in solution and solid form and, accordingly, are superior from a pharmacological viewpoint.

Preparation of the $\alpha,\alpha'$-dithiobis($\beta$-arylacrylic acids) of applicability herein is according to the methods described by E. Campaigne and P. E. Cline, J. Org. Chem. 21, 32 (1956) by oxidation of the corresponding $\alpha$-mercapto-$\beta$-arylacrylic acid with either iodine in ethanol or benzoyl peroxide in benzene according to the general scheme

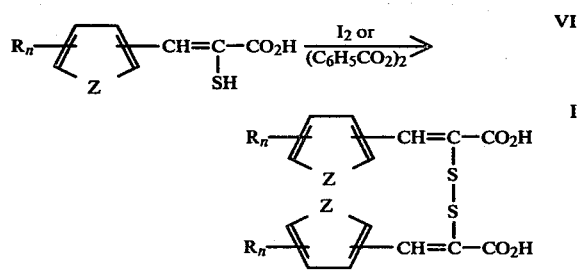

wherein Z, R and n are as defined hereinabove. Additionally, other oxidizing agents may be used in place of the iodine or benzoyl peroxide mentioned above such as hydrogen peroxide or molecular oxygen. The desired salts can be prepared by reaction between the hydroxide, carbonate or other basic metal, ammonium, or amine compound and the free $\alpha,\alpha'$-dithiobis($\beta$-arylacrylic acid) in the usual manner.

The following specific examples further illustrates the preparation and utility of compounds employed in the instant invention.

EXAMPLE 1

$\alpha,\alpha'$-Dithiobis[$\beta$-(2-furyl)acrylic acid]

Iodine is added to a solution of 100 g of potassium iodide in 500 ml of water to saturation. This saturated solution is added dropwise to a solution of $\alpha$-mercapto-$\beta$-(2-furyl)acrylic acid in 500 ml of acetonitrile and 30 ml of water until the color of iodine persists. The crude product which precipitates is recrystallized from methanol. M.P. 215° C.

EXAMPLE 2

α,α'-Dithiobis[β-(2-thienyl)acrylic acid]

Substituting α-mercapto-β-(2-thienyl)acrylic acid for α-mercapto-β-(2-furyl)acrylic acid in the procedure of Example 1 gives α,α'-dithiobis[β-(2-thienyl)acrylic acid].

EXAMPLE 3

α,α'-Dithiobis(β-phenylacrylic acid)

Substituting α-mercapto-β-phenylacrylic acid for α-mercapto-β-(2-furyl)acrylic acid in the procedure Example 1 gives α,α-dithiobis(β-phenylacrylic acid).

EXAMPLE 4

Zinc serum and tissue concentration enhancement

α,α'-Dithiobis[β-(2-furyl)acrylic acid] was administered to rats for seven days in 25 mg/kg p.o. daily doses. Three rats were killed each day until day 13. Zinc concentrations were measured in plasma, liver tissue, and kidney tissue. The data are summarized in Table 1.

TABLE 1

EFFECT OF α,α'-DITHIOBIS[β-(2-FURYL)ACRYLIC ACID] ON RAT PLASMA, KIDNEY AND LIVER ZINC CONCENTRATIONS

| Days After Initiation of Therapy | Plasma Zinc Concentration (μg Zn/ml) | Kidney Zinc Concentration (μg Zn/g) | Liver Zinc Concentration (μg Zn/g) | Dosage p.o. mg/kg |
|---|---|---|---|---|
| 0 | — | — | — | 25 |
| 1 | 10.1 ± 1.2 | 32.9 ± 1.4 | 32.0 ± 2.2 | 25 |
| 2 | 15.0 ± 2.0 | 37.4 ± 2.0 | 26.6 ± 0.4 | 25 |
| 3 | 14.7 ± 0.5 | 43.9 ± 1.6 | 31.7 ± 0.5 | 25 |
| 4 | 15.4 ± 0.1 | 47.7 ± 1.2 | 34.0 ± 0.5 | 25 |
| 5 | 18.6 ± 2.4 | 46.2 ± 1.5 | 35.5 ± 1.4 | 25 |
| 6 | 16.5 ± 0.7 | 52.0 ± 1.4 | 36.3 ± 4.7 | 25 |
| 7 | 16.9 ± 0.5 | 53.6 ± 1.5 | 33.6 ± 2.0 | 0 |
| 8 | 9.1 ± 1.1 | 43.3 ± 2.2 | 27.3 ± 1.1 | 0 |
| 9 | 5.1 ± 1.2 | 37.9 ± 1.5 | 30.0 ± 0.4 | 0 |
| 10 | 4.2 ± 1.2 | 33.3 ± 0.7 | 28.1 ± 1.2 | 0 |
| 11 | 3.0 ± 0.8 | 30.0 ± 2.0 | 28.2 ± 0.7 | 0 |
| 12 | 2.0 ± 0.4 | 29.4 ± 1.7 | 30.6 ± 0.6 | 0 |
| control | 1.5 ± 0.05 | 21.9 ± 0.3 | 27.3 ± 1.2 | 0 |

EXAMPLE 5

Zinc Serum Concentration Enhancement Single Dose Study

A single dose of α,α'-dithiobis[β-(2-furyl)acrylic acid] (25 mg/kg p.o.) is given to rats. Plasma zinc concentrations 1, 4 and 24 hours following administration were found to be 5.7, 11.5 and 10.8 Mg/L, respectively.

We claim:

1. A method of enhancing zinc serum and tissue levels in a patient in need thereof which comprises administering to said patient an effective amount of α,α'-dithiobis(β-arylacrylic acid) of the following formula

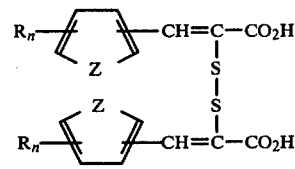

wherein Z is C=C, O, S or NH; R is H, $CH_3$, $C_2H_5$, OH, $CH_3O$, $C_2H_5O$, Cl, Br, F, L or $CF_3$; and n is 1, 2 or 3; or a pharmaceutically acceptable non-toxic salt thereof.

2. The method of claim 1 wherein R is H, $CH_3$, $C_2H_5$, OH, Cl, Br or $CF_3$.

3. The method of claim 2 wherein Z is O or S and the aromatic ring is substituted at the 2,5-positions.

4. The method of claim 1 wherein the active ingredient is α,α'-dithiobis [β-(2-furyl)acrylic acid] or a pharmaceutically acceptable non-toxic salt thereof.

5. The method of claim 1 wherein the active ingredient is α,α'-dithiobis[β-(2-thienyl)acrylic acid] or a pharmaceutically acceptable non-toxic salt thereof.

* * * * *